(12) United States Patent
Belardinelli et al.

(10) Patent No.: US 7,479,485 B2
(45) Date of Patent: *Jan. 20, 2009

(54) METHOD OF TREATING ARRHYTHMIAS

(75) Inventors: Luiz Belardinelli, Palo Alto, CA (US); Arvinder Dhalla, Mountain View, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 84 days.

This patent is subject to a terminal disclaimer.

(21) Appl. No.: 11/262,025

(22) Filed: Oct. 28, 2005

(65) Prior Publication Data

US 2006/0052333 A1   Mar. 9, 2006

Related U.S. Application Data

(62) Division of application No. 10/418,654, filed on Apr. 18, 2003, now Pat. No. 7,005,425.

(60) Provisional application No. 60/373,766, filed on Apr. 18, 2002.

(51) Int. Cl.
*A61K 31/7076* (2006.01)
*C07H 19/167* (2006.01)

(52) U.S. Cl. ...................... 514/46; 536/27.62

(58) Field of Classification Search .............. 514/46, 514/42, 43, 47, 44, 45, 262.1, 263.1, 263.2, 514/263.23, 256, 257, 258.1; 544/262, 264, 544/277; 536/27.3, 27.22, 25.32, 22.1, 28.5

See application file for complete search history.

(56) References Cited

U.S. PATENT DOCUMENTS 5,789,416 A * 8/1998 Lum et al. ............... 514/46
5,998,387 A * 12/1999 Belardinelli et al. ........ 514/46
6,605,597 B1 * 8/2003 Zablocki et al. ............ 514/46
6,946,449 B2 * 9/2005 Elzein et al. .............. 514/46

OTHER PUBLICATIONS

Wu et al. "A partial agonist of the A1-adenosine receptor selectively slows AV conduction in guninea pig hearts." Am. J. Phsiol. Heart Circ. Phsiol., 280(1), H334-343, Jan. 2001.*
GMO Manual: Clinical Section: Cardiovascular Disorders, Dept. of Navy, Bureau of Medicine and Surgery (1999).*
2006 Chemical Abstracts Service Catalog, published by Chemical Abstracts Service, p. 52.*
Avery's Drug Treatment: Principles and Practice of Clinical Pharmacology and Therapeutics, 3rd Edition, 1987, Edited by Trevor M. Speight, Chapter VIII, pp. 255-282.*
Belardinelli et al., "The Cardiac Effects of a Novel A1-Adenosine Receptor Agonist in Guinea Pig Isolated Heart" The Journal of Pharmacology and Experimental Therapeutics (1994) vol. 271, No. 3, pp. 1371-1382.*
FDA approval package for Esmolol hydrochloride in sodium chloride, NDA 19-386/S004 and NDA 19-386/S-006, available online as www.fda.gov.*
FDA approval package for Esmolol hydrochloride in sodium chloride, NDA 19-386/S004 and NDA 19-386/S-006, approved and published Aug. 15, 1998, available online as www.fda.gov.*

* cited by examiner

*Primary Examiner*—Shaojia Anna Jiang
*Assistant Examiner*—Eric S Olson

(57) ABSTRACT

Methods are provided for treating arrhythmia in a manner that minimizes undesirable side effects, comprising administration of a therapeutically effective minimal dose of an $A_1$ adenosine receptor agonist with a therapeutically effective minimal dose of a beta blocker, calcium channel blocker, or a cardiac glycoside.

5 Claims, 5 Drawing Sheets

METHOD OF TREATING ARRHYTHMIAS

This application is a Divisional of U.S. patent application Ser. No. 10/418,654, filed Apr. 18, 2003, now issued as U.S. Pat. No. 7,005,425, which claims priority to U.S. Provisional Patent Application Ser. No. 60/373,766, filed Apr. 18, 2002.

FIELD OF THE INVENTION

This invention relates to a method of treating arrhythmias and heart failure in a manner that minimizes undesirable side effects, comprising administration of a low dose of an adenosine Al receptor agonist in conjunction with a low dose of a beta blocker, or a calcium channel blocker, or a cardiac glycoside.

BACKGROUND INFORMATION

Arrhythmias are abnormal heart rhythms that occur either in the atria or the ventricles. Arrhythmias arising in the atria are called atrial arrhythmias, and these disorders include atrial fibrillation, atrial flutter, and paroxysmal atrial tachycardia (PSVT). Arrhythmias arising in the ventricles, known as ventricular arrhythmias, are a group of disorders having diverse etiologies, including idiopathic ventricular tachycardia, ventricular fibrillation, and Torsade de Pointes (TdP). Arrhythmias can range from incidental, asymptomatic clinical findings to life-threatening abnormalities, and account for a significant percentage of the causes of death in humans. Thus, it is desirable to develop methods of mitigating the effects of arrhythmias.

A variety of anti-arrhythmic drug therapies are presently available, and are classified as follows. Class I anti-arrhythmics, comprising sodium channel blockers; Class II, comprising beta-blockers; Class III, comprising drugs that prolong action potential (usually by blocking potassium channels); and Class IV, comprising calcium channels blockers. Cardiac glycosides, for example digitalis, are also used as drugs for the treatment of arrhythmia, but they have a delayed onset of action (about 30 minutes) and their peak effects are not observed for ≧3 to 4 hours after administration. Additionally, digitalis is toxic at doses close to the therapeutic dose, which limits the utility of the compound.

In fact all of the above classes have significant limitations. For example, beta-blockers, such as propranolol and esmolol, and calcium-channel blockers, for example verapamil, bepridil, and diltiazem, can cause hypotension, potentially have negative inotropic effects, and may also precipitate new arrhythmias, including TdP.

Adenosine, which is widely found in nature, is another compound that has anti-arrhythmic activities, by virtue of its ability, at certain dose levels, to slow the conduction in the atrioventricular node. The anti-arrhythmic effects of adenosine are due exclusively to its interaction with the adenosine $A_1$ receptor subtype. However, although adenosine is highly effective in ameliorating arrhythmia, it also binds contemporaneously to other adenosine receptor subtypes ($A_{2A}$, $A_{2B}$, and $A_3$), which results in undesirable side effects, such as vasodilation, changes in the heart rate, mast cell degradation, etc. Adenosine also has a short half-life (~10 sec), making it ineffective in treating conditions that require prolonged action.

Compounds that are selective agonists for adenosine $A_1$ receptors are known. For example, a new class of agonists that bind to adenosine $A_1$ receptors and that are useful in treating arrhythmias are disclosed in U.S. Pat. No. 5,789,416, and in U.S. patent application, Ser. No, 10/194,335, the entire disclosures of which are hereby incorporated by reference. These compounds have a high specificity for the adenosine $A_1$ receptor subtype, but like all therapeutic compounds, can potentially cause side effects.

Antiarrythymic agents in general have a narrow margin between the dose required to produce the desired antiarrhythmic effect and the dose that produces an adverse effect. It would therefore be desirable to find a method of treating arrhythmia that is effective at low doses (or minimal doses) of the active agent, thus decreasing the likelihood of adverse effects. We have discovered that low doses of adenosine $A_1$ receptor agonists, preferably partial agonists, and more preferably selective adenosine $A_1$ receptor agonists, can be used in combination with low doses of beta blocker, calcium channel blockers, or cardiac glycosides, to provide an effective treatment for arrhythmia that minimizes the side effects of beta blockers, calcium channel blockers, cardiac glycosides, and $A_1$-adenosine receptor agonists that may potentially occur when taken individually. It has also been observed that at low doses, the combination of these agents act in a synergistic manner, thus reducing even further the chance of side effects. It has also been observed that the combination of an $A_1$ adenosine receptor antagonist with a beta blocker can be used in the treatment of heart failure, including ischemic heart disease, congestive heart failure, heart failure syndrome, hypertension, and the like.

Accordingly, a novel and effective method of treating arrhythmias is provided that restores sinus rhythm without slowing the sinus rate and is virtually free of undesirable side effects, such as changes in mean arterial pressure, blood pressure, increased heart rate, TdP, or other adverse effects.

SUMMARY OF THE INVENTION

It is an object of this invention to provide an effective method of treating arrhythmias in a mammal while minimizing undesirable side effects. Accordingly, in a first aspect, the invention relates to a method of treating arrhythmias in a mammal, comprising administration of a therapeutically effective minimal dose of an $A_1$ adenosine receptor agonist in conjunction with a therapeutically effective minimal dose of a beta blocker, calcium channel blocker, or a cardiac glycoside to a mammal in need thereof.

In one embodiment, an $A_1$-adenosine receptor agonist useful for this invention is a compound of Formula I:

Formula I wherein:

$R_1$ is an optionally substituted heterocyclic group, preferably monocyclic. The effective dose is preferably in the range of 0.0001-0.05 mg/kg, more preferably 0.0005-0.02 mg/kg.

In a preferred embodiment, $R^1$ is 3-tetrahydrofuranyl, 3-tetrahydrothiofuranyl, 4-pyranyl, or 4-thiopyranyl. The most preferred compound of Formula I is 6-(3-(R)—N-aminotetrahydrofuranyl)purine riboside (hereinafter referred to as CVT-510).

In another embodiment, an $A_1$-adenosine receptor agonist useful for this invention is a compound of Formula II:

Formula II wherein:
$R^1$ is optionally substituted alkyl, optionally substituted cycloalkyl, optionally substituted aryl, or optionally substituted heteroaryl;
$R^2$ is hydrogen, halo, trifluoromethyl, optionally substituted acyl, or cyano;
$R^3$ is optionally substituted alkyl, optionally substituted cycloalkyl, optionally substituted aryl; optionally substituted heteroaryl, or optionally substituted heterocyclyl,
$R^4$ and $R^5$ are independently hydrogen or optionally substituted acyl; and
X and Y are independently a covalent bond or optionally substituted alkylene.

The effective dose is preferably in the range of 0.1 to 200 mg/kg, more preferably 0.5 to 50 mg/kg.

The most preferred compound of Formula II is one in which $R^1$ is 2-hydroxycyclopentyl, X and Y are covalent bonds, $R^2$, $R^3$, and $R^4$ are hydrogen, and $R^5$ is 2-fluorophenyl, most preferably 2-{6-[((1R,2R)-2-hydroxycyclopentyl)amino]purin-9-yl}(4S,5S,3R)-5-[(2-fluorophenylthio)methyl]oxolane-3,4-diol, hereinafter referred to as CVT-3619.

Preferred beta blockers include atenolol, esmolol, sotalol, and propranolol. More preferred is esmolol. The preferred effective dose is in the range of 0.01 to 100 mg/kg, more preferably in the range of 0.1 to 10 mg/kg.

Preferred calcium channel blockers include amlodipine, bepridil, diltiazem, felodipine, isradipine, nicardipine, nifedipine, nimodipine and verapamil. The preferred effective dose is in the range of 0.01 to 50 mg/kg, more preferably in the range of 0.1 to 10 mg/kg.

Preferred cardiac glycosides include digoxin and digitoxin.

One preferred embodiment of the invention is a method of treating arrhythmias in a mammal comprising administering a therapeutically effective minimal dose of CVT-510 in conjunction with a therapeutically effective minimal dose of a beta blocker, preferably esmolol, atenolol, sotolol or propranol, more preferably esmolol, to a mammal in need thereof.

Another preferred embodiment of the invention is a method of treating arrhythmias in a mammal comprising administering a therapeutically effective minimal dose of CVT-3619, and a therapeutically effective minimal dose of a beta blocker, preferably esmolol, atenolol, sotolol or propranol, more preferably esmolol, to a mammal in need thereof.

Another preferred embodiment of the invention is a method of treating arrhythmias in a mammal comprising administering a therapeutically effective minimal dose of CVT-510, or a therapeutically effective minimal dose of CVT-3619, in conjunction with a therapeutically effective minimal dose of a calcium channel blocker, preferably verapamil, to a mammal in need thereof.

A third preferred embodiment of the invention is a method of treating arrhythmias in a mammal comprising administering a therapeutically effective minimal dose of CVT-510, or a therapeutically effective minimal dose of CVT-3619, in conjunction with a therapeutically effective minimal dose of a cardiac glycoside, preferably digoxin, to a mammal in need thereof.

In another aspect, the invention relates to a pharmaceutical composition useful for treating arrhythmias in a mammal, comprising a therapeutically effective minimal dose of an $A_1$ adenosine receptor agonist and a therapeutically effective minimal dose of a beta blocker, and at least one pharmaceutically acceptable excipient.

One preferred embodiment of the invention is a pharmaceutical composition for treating arrhythmias in a mammal, comprising a therapeutically effective minimal dose of a compound of Formula I, more preferably CVT-510, and a therapeutically effective minimal dose of a beta blocker, preferably esmolol, atenolol, sotolol or propranol, more preferably esmolol, to a mammal in need thereof. The Formula I dose is preferably in the range of 0.0001-0.05 mg/kg, more preferably 0.0005-0.02 mg/kg, and the beta blocker dose is in the in the range of 0.01 to 100 mg/kg, more preferably in the range of 0.1 to 10 mg/kg.

Another preferred embodiment of the invention is a pharmaceutical composition for treating arrhythmias in a mammal, comprising a therapeutically effective minimal dose of a compound of Formula II, more preferably CVT-3619, and a therapeutically effective minimal dose of a beta blocker, preferably esmolol, atenolol, sotolol or propranol, more preferably esmolol, to a mammal in need thereof. The dose is preferably in the range of 0.1 to 200 mg/kg, more preferably 0.5 to 25 mg/kg, and the beta blocker dose is in the in the range of 0.01 to 100 mg/kg, more preferably in the range of 0.1 to 10 mg/kg.

In another aspect, the invention relates to a method of treating heart failure in a mammal, comprising administration of a therapeutically effective minimal dose of an $A_1$ adenosine receptor agonist in conjunction with a therapeutically effective minimal dose of a beta blocker to a mammal in need thereof.

ABBREVIATIONS

BPM: beats per minute
HR: Heart rate
SH: Stimulus to His (length of time for conduction of current through AV node)
PSVT Paroxysmal Atrial Tachycardia Definitions and General Parameters As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl,n-decyl, tetradecyl, and the like.

The term "substituted alkyl" refers to:
1) an alkyl group as defined above, having from 1 to 5 substituents, preferably 1 to3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or
2) an alkyl group as defined above that is interrupted by 1-5 atoms or groups independently chosen from oxygen, sulfur and —NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or
3) an alkyl group as defined above that has both from 1 to 5 substituents as defined above and is also interrupted by 1-5 atoms or groups as defined above.

The term "lower alkyl" refers to a monoradical branched or unbranched saturated hydrocarbon chain having from 1 to 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1 to 3 substituents, as defined for substituted alkyl, or a lower alkyl group as defined above that is interrupted by 1-5 atoms as defined for substituted alkyl, or a lower alkyl group as defined above that has both from 1 to 5 substituents as defined above- and is also interrupted by 1-5 atoms as defined above.

The term "alkylene" refers to a diradical of a branched or unbranched saturated hydrocarbon chain, preferably having from 1 to 20 carbon atoms, preferably 1-10 carbon atoms, more preferably 1-6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, preferably having from 1 to 6 carbon atoms.

The term "substituted alkylene" refers to:
(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or
(2) an alkylene group as defined above that is interrupted by 1-5 atoms or groups independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or
(3) an alkylene group as defined above that has both from 1 to 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—),1-ethoxy-2-(2-ethoxy-ethoxy)ethane (—CH$_2$CH$_2$O—CH$_2$—OCH$_2$CH$_2$—OCH$_2$CH$_2$—), and the like.

The term "aralkyl: refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is; optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "alkylthio" refers to the group R-S-, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl (—CH═CH$_2$), 1-propylene or allyl (—CH$_2$CH═CH$_2$), isopropylene (—C(CH$_3$)

═CH₂), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO₂-alkyl, SO₂-aryl and —SO₂-heteroaryl. All substituents may be optionally further substituted by alkyl, alkoxy, halogen, CF₃, amino, substituted amino, cyano, or —S(O)$_n$R, in which R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl, (—C≡CH), propargyl (or propynyl, —C≡CCH₃), and the like. In the event that alkynyl is attached to nitrogen, the triple bond cannot be alpha to the nitrogen.

The term "substituted alkynyl" refers to an alkynyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO₂-alkyl, SO₂-aryl and —SO₂-heteroaryl. All substituents may be optionally further substituted by alkyl, alkoxy, halogen, CF₃, amino, substituted amino, cyano, or —S(O)$_n$R, in which R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). All substituents may be optionally further substituted by alkyl, alkoxy, halogen, CF₃, amino, substituted amino, cyano, or —S(O)$_n$R, in which R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF₃, amino, substituted amino, cyano, or —S(O)$_n$R, in which R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. All substituents may be optionally further substituted by alkyl, alkoxy, halogen, CF₃, amino, substituted amino, cyano, or —S(O)$_n$R, in which R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO₂-alkyl, SO₂-aryl and —SO₂-heteroaryl. All substituents may be optionally further substituted by alkyl, alkoxy, halogen, CF₃, amino, substituted amino, cyano, or —S(O)$_n$R, in which R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH₂.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y-Z, in which Y is optionally substituted alkylene and Z is alkenyl, cycloalkenyl, or alkynyl,. All substituents may be optionally further substituted by alkyl, alkoxy, halogen, CF₃, amino, substituted amino, cyano, or —S(O)$_n$R, in which R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, CF₃, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO₂-alkyl, SO₂-aryl and —SO₂-heteroaryl. All substituents may be optionally further substituted by alkyl, alkoxy, halogen, CF₃, amino, substituted amino, cyano, or —S(O)$_n$R, in which R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The terms "compound of Formula I" and "compound of Formula II" are intended to encompass the compounds of the invention as disclosed, and the pharmaceutically acceptable salts, pharmaceutically acceptable esters, and prodrugs of such compounds.

The term "therapeutically effective amount" refers to that amount of an active ingredient (A$_1$-agonist, beta-blocker, calcium channel blocker, cardiac glycoside) that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by a prescribing physician.

The term "therapeutically effective minimal dose" or "low dose" of an A$_1$ adenosine receptor agonist refers to a dose level of an A$_1$ adenosine receptor agonist that is generally considered to be below the therapeutically effective amount as defined above, but is sufficient to provide effective treatment when administered in conjunction with a "therapeutically effective minimal dose" or "low dose" of a beta blocker, calcium channel blocker, or a cardiac glycoside. For example, a therapeutically effective minimal dose of CVT-3619 is one that would not normally be considered to be useful in the treatment of arrhythmia, but is now found to be useful in the treatment of arrhythmia when administered in conjunction with a therapeutically effective minimal dose of a beta blocker, because of the synergistic effect obtained upon combining an A$_1$-agonist with a beta blocker. The therapeutically effective minimal dose will vary depending upon the subject and disease condition being treated, the weight and age of the subject, the severity of the disease condition, the manner of administration and the like, which can readily be determined by a prescribing physician.

A therapeutically effective minimal dose of an adenosine A$_1$ receptor agonist is administered "in conjunction with" a therapeutically effective minimal doses of a beta blocker, or a calcium channel blocker, or a cardiac glycoside. In this context, the word "conjunction" means that the doses may be administered together at the same time, for example in a single pill or solution, or administered separately at the same time, or administered at different times.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

As used herein, the term "agonist" refers to the ability of a compound to interact with a receptor and evoke a maximal effect. This effect is known as the intrinsic efficacy. In contrast, "partial agonists" interact with adenosine $A_1$ receptors but produce a less than maximal response.

The term "adenosine $A_1$ receptor agonist" refers to an agent that binds to adenosine $A_1$ receptors thereby producing a negative dromotropic effect. For example, CVT-3619 is a partial $A_1$-adenosine receptor agonist—it has a rate dependent effect upon AV nodal conduction. It increases AV-node refractoriness, and thus reduces ventricular rate during atrial tachyarrhythmia. $A_1$ agonists also act to inhibit the release of norepinephrine from the pre-synaptic nerve terminal, and to inhibit the uptake of norepinephrine at the post-synaptic nerve terminal.

The term "beta-blocker" refers to an agent that binds to a beta-adrenergic receptor and inhibits the effects of beta-adrenergic stimulation. Beta-blockers increase AV nodal conduction. In addition, Beta-blockers decrease heart rate by blocking the effect of norepinephrine on the post synaptic nerve terminal that controls heart rate. Beta blockers also decrease intracellular $Ca^{++}$ overload, which inhibits after-depolarization mediated automaticity. Examples of beta blockers include atenolol, esmolol, sotalol, propranolol, bopindolol, carteolol, oxprenolol, penbutolol, carvedilol, medroxalol, bucindolol, levobunolol, metipranolol, betaxolol, celiprolol, and propafenone.

The term "calcium channel blocker" refers to an agent that blocks voltage-dependent "L-type calcium channel. They are used in treatment of heart diseases, including cardiac arrhythmia—they have a rate dependent effect upon AV nodal conduction. Examples of calcium channel blockers include amlodipine, bepridil, diltiazem, felodipine, isradipine, nicardipine, nifedipine, nimodipine and verapamil.

The term "cardiac glycoside" refers to a compound with a steroidal nucleus and a lactone ring, and usually has one or more sugar residues. They are used in treatment of heart diseases, including cardiac arrhythmia—they have a rate dependent effect upon AV nodal conduction. Examples of cardiac glycosides include digoxin and digitoxin.

The term "synergistic" effect means a result produced by a combination of drugs that is greater than that produced by each drug alone.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "compound of Formula I", or "compound of Formula II" is intended to encompass the compounds of the invention as disclosed, and the pharmaceutically acceptable salts, pharmaceutically acceptable esters, and prodrugs of such compounds. Additionally, the compounds of the invention may possess one or more asymmetric centers, and can be produced as a racemic mixture or as individual enantiomers or diastereoisomers. The number of stereoisomers present in any given compound of the invention depends upon the number of asymmetric centers present (there are 2n stereoisomers possible where n is the number of asymmetric centers). The individual stereoisomers may be obtained by resolving a racemic or non-racemic mixture of an intermediate at some appropriate stage of the synthesis, or by resolution of the compound of Formula I or Formula II by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

Pharmaceutical Compositions

The two components of the invention, an $A_1$-adenosine receptor agonist and a beta-blocker, calcium channel blocker, or a cardiac glycoside, may be administered as a pharmaceutical composition that contains a physical mixture of the two components, but is preferably administered as two separate pharmaceutical compositions. Such separate compositions are preferably administered concurrently, but may also be administered at different times. This invention therefore provides pharmaceutical compositions that contain, as the active ingredient, one or two of the components, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modem Pharmaceutics", Marcel Dekker, Inc. $3^{rd}$ Ed. (G. S. Banker & C. T. Rhodes, Eds.).

Administration

The components may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the component in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the components. Administration may be via capsule or enteric coated tablets, or the like. In making the pharmaceutical compositions that include at least one compound of Formula I or II, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I and II are effective over a wide dosage range and is generally administered in a pharmaceutically effective amount. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage element, the latter being in the form of an envelope over the former. The two elements can be separated by an enteric layer that serves to resist disintegration in the stomach and permit the inner element to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

The beta blockers, calcium channel blockers, and cardiac glycosides of this invention are well known in the art, and are commercially available. The compounds of Formula I may be prepared by conventional methods, in the manner disclosed in U.S. Pat. No. 5,789,416, the entire disclosure of which is hereby incorporated by reference. For example, the preferred compound CVT-510 is prepared as follows.

Example 1

A. Preparation of (3-(S)-aminotetrahydrofuranyl)purine riboside

Step 1. Resolution of 3-(S)-aminotetrahydrofuran

A mixture of 3-aminotetrahydrofuran hydrochloride (0.5 GM, 4 mmol) and (S)-(+)-10-camphorsulfonyl chloride (1.1 gm, 4.4 mmol) in pyridine (10 ml) was stirred for 4 hours at room temperature and then concentrated. The residue was dissolved in ethyl acetate and washed with 0.5N hydrochloric acid, followed by sodium bicarbonate and then brine. The organic layer was dried over magnesium sulfate, filtered, and solvent removed from the filtrate under reduced pressure to provide 1.17 g of a brown oil, which was chromatographed on silica gel (25% to 70% ethyl acetate/hexanes). The white solid obtained was repeatedly recrystallized from acetone to yield the (S)-camphorsulfonate of 3-(S)-aminotetrahydrofuran.

Step 2. Preparation of 3-(S)-aminotetrahydrofuran hydrochloride

The (S)-camphorsulfonate of 3-(S)-aminotetrahydrofuran (170 mg, 0.56 mmol) was dissolved in concentrated hydrochloric acid/acetic acid (2 mL each), and stirred for 20 hours at room temperature. The reaction mixture was washed three times with methylene chloride (10 ml), and the combined extracts concentrated to dryness under reduced pressure, to give 75 mg of 3-(S)-aminotetrahydrofuran, as a white solid.

Step 3. Preparation of 6-(3-(S)-aminotetrahydrofuranyl)purine riboside

A mixture of 6-chloropurine riboside (30 mg, 0.10 mmol), 3-(S)-aminotetrahydrofuran hydrochloride (19 mg, 0.15 mmol), and triethylamine (45 ml, 0.32 mmol) in methanol (0.5 ml) was heated to 80° C. for 18 hours. The mixture was cooled, concentrated and chromatographed with 95/5 (methylene chloride/methanol), to give 8 mg of 6-(3-(S)-aminotetrahydrofuranyl)purine riboside, as a white solid.

B. Preparation of (3-(R)-aminotetrahydrofuranyl)purine riboside (CVT-510)

Similarly, following steps 1-3 above, but replacing (S)-(+)-10-camphorsulfonyl chloride with (R)-(−)-10-camphorsulfonyl chloride, the following compound was prepared:

6-(3-(R)-aminotetrahydrofuranyl)purine riboside (CVT-510).

Similarly, other enantiomers of the compounds of Formula I are prepared.

The compounds of Formula II may be prepared by conventional methods, in the manner disclosed in U.S. patent application Ser. No. 10/194,335, the entire disclosure of which is hereby incorporated by reference. For example, the preferred compound CVT-3619 is prepared as follows.

Example 2

Preparation of 6-(6-Chloropurine-9-yl)-2,2-dimethyltetrahydrofuro[3,4-d][1,3]dioxol-4-yl]methanol (2)

To a solution of 2-(6-chloropurin-9-yl)-5-hydroxymethyltetrahydrofuran-3,4-diol (a compound of formula (1)) (4.9 g, 17.1 mmol) and 2,2-dimethoxypropane (10.5 mL, 84.7 mmol) in dimethylformamide (100 mL) was added p-toluenesulfonic acid (325 mg, 1.71 mmol). After stirring for 24 hours at 70° C., the reaction was concentrated in vacuo and the residue purified by flash column chromatography (70% EtOAc/Hexanes) to give 6-(6-chloropurine-9-yl)-2,2-dimethyltetrahydrofuro[3,4-d][1,3]dioxol-4-yl]methanol, a compound of formula (2), as an off-white solid (2). (3.8 g, 68%) $^1$H NMR (CDCl3) δ 1.4 (s, 3H), 1.65 (s, 3H), 3.8-4.0 (dd, 2H), 4.6 (s, 1H), 5.1-5.3 (m, 2H), 6.0 (d, 1H), 8.25 (s, 1H), 8.8 (s, 1H).

Example 3

Preparation of 1-{[(2S,1R,4R,5R)-4-(6-chloropurin-9-yl)-7,7-dimethyl-3,6,8-trioxabicyclo[3.3.0]oct-2-yl]methylthio}-2-fluorobenzene (3)

To a solution of 6-(6-chloropurine-9-yl)-2,2-dimethyltetrahydrofuro[3,4-d][1,3]dioxol-4-yl]methanol, a compound of formula (2) (0.48 g, 1.47 mmoles) in 20 mL of tetrahydrofuran was added triphenylphosphine (0.77 g, 2.94 mmoles) and diethylazodicarboxylate (0.47 mL, 2.94 mmoles), and the mixture stirred for 5 minutes. 2-Fluorothiophenol (0.31 mL, 2.94 mmoles) was then added, and the mixture was stirred under reflux. After 72 hours of reflux, the reaction was concentrated in vacuo and the residue purified by flash column chromatography (20%EtOAc/Hexanes) to give 1-{[(2S,1R,4R,5R)-4-(6-chloropurin-9-yl)-7,7-dimethyl-3,6,8-trioxabicyclo[3.3.0]oct-2-yl]methylthio}-2-fluorobenzene, a compound of formula (3), as a clear viscous oil (3). (0.25 g, ~40%) $^1$H NMR (CDCl3) δ 1.4 (s, 3H), 1.6 (s, 3H), 3.2 (m, 2H), 4.6 (t, 1H), 5.1 (m, 1H), 5.5 (m, 1H), 6.0 (d, 1H), 7.0 (m, 2H), 7.2 (m, 1H), 7.4 (m, 1H), 8.25 (s, 1H), 8.75 (s, 1H).

Example 4

Preparation of (9-{(4S,1R,2R5R)-4-[(2-fluorophenylthio)methyl]-7,7-dimethyl-3,6,8-trioxabicyclo[3.3.0]oct-2-yl}purin-6-yl)cyclopentylamine To a solution of 1-{[(2S,1R,4R,5R)-4-(6-chloropurin-9-yl)-7,7-dimethyl-3,6,8-trioxabicyclo[3.3.0]oct-2-yl]methylthio}-2-fluorobenzene, a compound of formula (3), (0.125 g, 2.86 mmoles) in 10 mL of ethanol and 1 mL of triethylamine was added cyclopentylamine in excess, and the mixture refluxed under nitrogen for 24 hours. The solvent was removed under reduced pressure, and the residue was purified by preparative TLC using 1:1 EtOAc:Hexanes to give (9-{(4S,1R,2R,5R)-4-[(2-fluorophenylthio)methyl]-7,7-dimethyl-3,6,8-trioxabicyclo[3.3.0]oct-2-yl}purin-6-yl)cyclopentylamine, a compound of formula (4), as a yellow oil (80 mg, 56%) $^1$H NMR (CDCl3) δ 1.4 (s, 3H), 1.6 (s, 3H), 1.6-2.4 (m, 6H), 3.15-3.25 (m, 2H), 4.1 (bs, 1H), 4.4 (t, 1H), 5.1 (m, 1H), 5.5 (m, 1H), 6.0 (d, 1H), 6.2 (bs, 1H), 7.0 (m, 2H), 7.2 (m, 1H), 7.4 (m, 1H), 7.8 (s, 1H), 8.25 (s, 1H).

Example 5

Preparation of (4S,5S,3R)-2-[6-(cyclopentylamino)purin-9-yl]-5-[(2-fluorophenylthio)methyl]oxolane-3,4-diol Formula I (9-{(4S,1R,2R,5R)-4-[(2-fluorophenylthio)methyl]-7,7-dimethyl-3,6,8-trioxabicyclo[3.3.0]oct-2-yl}purin-6-yl)cyclopentylamine, a compound of formula (4) (50 mg) was dissolved in a mixture of acetic acid (8 mL) and water (2 mL) and heated at 90 C for 16 hours. Solvents were removed under reduced pressure, and the residue was purified by preparative TLC [methanol-dichloromethane(1:9)] to afford (4S,5S,3R)-2-[6-(cyclopentylamino)purin-9-yl]-5-[(2-fluorophenylthio)methyl]oxolane-3,4-diol, a compound of Formula I. $^1$H NMR (CDCl3) δ 1.6-2.4 (m, 6H), 3.15-3.25 (m, 2H), 4.1 (bs, 1H), 4.4-4.65 (m, 4H), 6.0 (d, 1H), 6.8 (bs, 1H), 7.05 (m, 2H), 7.2 (m, 1H), 7.4 (m, 1H), 7.8 (s, 1H), 8.25 (s, 1H).

Example 6

Studies in Awake Rats

Methods

Rats (Sprague Dawley) weighing 300-400 gms were purchased from Simonsen laboratories. CVT-3619 was dissolved in DMSO and further diluted in saline. CVT-510 was dissolved in saline. Ketamine was purchased from Fort Dodge Animal Health, Xylazine from Bayer and Acepromazine Maleate from Fermenta Animal Health Co. Metoprolol and propranolol were purchased from SIGMA. Esmolol was obtained from a local pharmacy.

Telemetry Studies

For these studies, rats were instrumented with radiotelemetered transmitters (Data Sciences) at least 3 weeks prior to experimentation. Animals were anesthetized by peritoneal injection of a "cocktail" (1 ml/kg) containing Ketamine (75 mg/ml), Xylazine (5 mg/ml), and Acepromazine (1 mg/ml). After 20-30 minutes of induction of anesthesia, a midline laparotomy was performed. The transmitter for recordings of ECG, blood pressure and body temperature was placed in the abdominal cavity, and secured to the abdominal muscles. Two electrocardiographic leads were tunneled through the subcutaneous—one toward the upper left shoulder and the other to the right thigh, and secured with sutures. A fluid filled sensor catheter was inserted in the descending aorta above the iliac bifurcation for measurement of blood pressure. The tip of the telemetry catheter was located in the abdominal aorta just caudal to the renal arteries. Once the transmitter and leads were in place and determined to be functioning properly, the abdominal wall was sutured. After recovery from anesthesia, the rats were housed individually in cages placed on their respective receivers. The ECG, blood pressure and temperature were recorded and heart rate measured by a Dataquest ART Gold system (Version 2.2; Data Sciences Intl). The system consisted of a transmitter, i.e., biopotential sensor (Model TL11M2-C50-PXT), receivers (Model RPC-1), a consolidation matrix (BCM 100), a personal computer (Compaq DeskPro Series 3574) and Dataquest 4 software. Heart rate, blood pressure and temperature were measured at 5-minute intervals. Each recording lasted 10 seconds and all cardiac cycles within this period were averaged. Animals were given various drugs in a randomized manner after recording the baseline data for at least two hours.

Implantation of Osmotic Pump

A subgroup of animals was implanted with osmotic pumps containing CVT-510 for combination experiments. After 7 days or more of having been implanted with radio-telemetry transmitters for recording ECG (L-2), and verifying that the transmitters were functioning, each rat was implanted with an Alzet mini-osmotic pump. Under anesthesia (see above) and sterile conditions, one Alzet mini-osmotic pump, was implanted subcutaneously (SC) in the interscapular area of each rat. The osmotic pumps were filled with either vehicle or CVT-510 (to deliver a dose of 20 μg/kg/hr).

Surgical Insertion of Catheters for Determining Plasma Concentrations

Carotid artery was catheterized to obtain serial blood samples for the analysis of CVT-510 plasma concentrations. Animals were anesthetized by peritoneal injection of a "cocktail" (1 ml/kg) containing Ketamine (75 mg/ml), Xylazine (5 mg/ml), and Acepromazine (1 mg/ml). After a 20-30 min. of induction of anesthesia, a midline incision was made in the neck region to expose the external carotid artery. A tunnel is made for the catheter using blunt dissection in the subcutaneous pocket on the dorsal section of the neck where it is externalized. The carotid artery was cannulated with 24-gauge catheters sampling of blood for determination of plasma levels of CVT-510. Externally, the catheter is tied at the back of the neck and a piece of suture is tied around the knot leaving both ends about 2 inches long for retrieval from under the skin. The knotted catheter is retracted back under the skin to prevent being pulled out by the rat. The incision is then cleaned with saline, closed with wound clips, and an antibiotic (0.4 ml of a 40 mg/ml solution of gentamicin) is given I.V. Animals were allowed to recover for at least 48 hrs before performing the experiment. On the day of the experiment, an injection plug was attached to a 19-gauge IV set, filled with 0.1% heparinized saline and the needle end was inserted into the catheters. Animals were given either a saline or metoprolol injection 1 hr prior to CVT-510 injection. About 400 μl of blood was drawn from the line in the carotid artery and 400 μl saline flushed in to replace blood volume at predetermined time points. Plasma was separated and saved at −80° C. for analysis of CVT-510 levels.

Determination of Plasma Concentrations of CVT-510

CVT-510 plasma level analysis was performed as follows. Briefly, 50 μL of plasma sample was precipitated with 400 μL of acetonitrile:methanol (90:10) containing internal standard. The filtrates were evaporated to dryness and reconstituted in 100 μL of 90:10 water:methanol. Concentration of CVT-510 in protein precipitation filtrates were analyzed by LC-MS-MS using a Waters Alliance 2690 HPLC system (Millford, Mass.) coupled to a Waters/Micromass Quattro Ultima triple quadrupole mass spectrometer (Millford, Mass.). Calibration curves were constructed by plotting peak area ratios of the analyte to internal standard against concentration, using a weighted (1/X) linear regression model in all instances.

Data Analysis

The slowing of heart rate caused by each treatment was quantified by determining the area under the curve (AUC), using the trapezoidal method for calculations. Data used for analysis was the area under/over the curve calculated using change form baseline data (untreated animals). The data was analyzed for the magnitude as well as the duration of bradycardia caused by each treatment. The AUC values for various doses for each monotherapy were compared using one-way ANOVA followed by Tukey's test for multiple comparisons. The significance level was set at $p<0.05$ for all comparisons.

The results obtained from the above studies are shown in Figure form, as follows.

Figure 1:
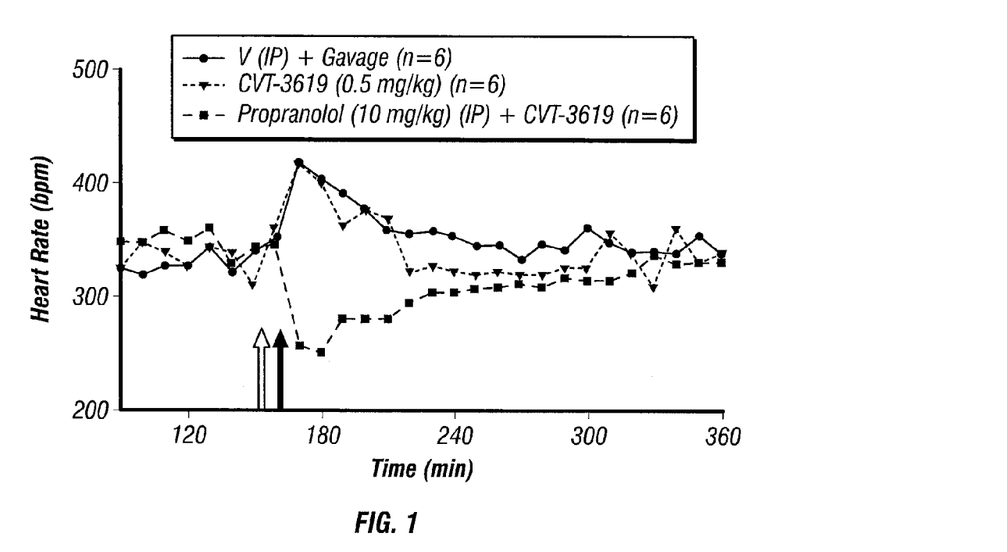
FIG. 1. Comparison of the effect of CVT-3619 alone and CVT-3619 in combination with propranolol on heart rate.

FIG. 1 shows the effect of CVT-3619 (a partial $A_1$ receptor agonist) on heart rate with and without propranolol in awake rats instrumented with telemetry radiotransmitters. CVT-3619 at dose of (0.5 mg/kg, ip) by itself had minimal effect on heart rate. However when given in the presence of a beta blocker (propranolol, 10 mg/kg, ip), there is significant lowering of heart rate below baseline as compared to CVT-3619 alone. Propranolol was given 10 minutes prior to CVT-3619 injection.

Figure 2:
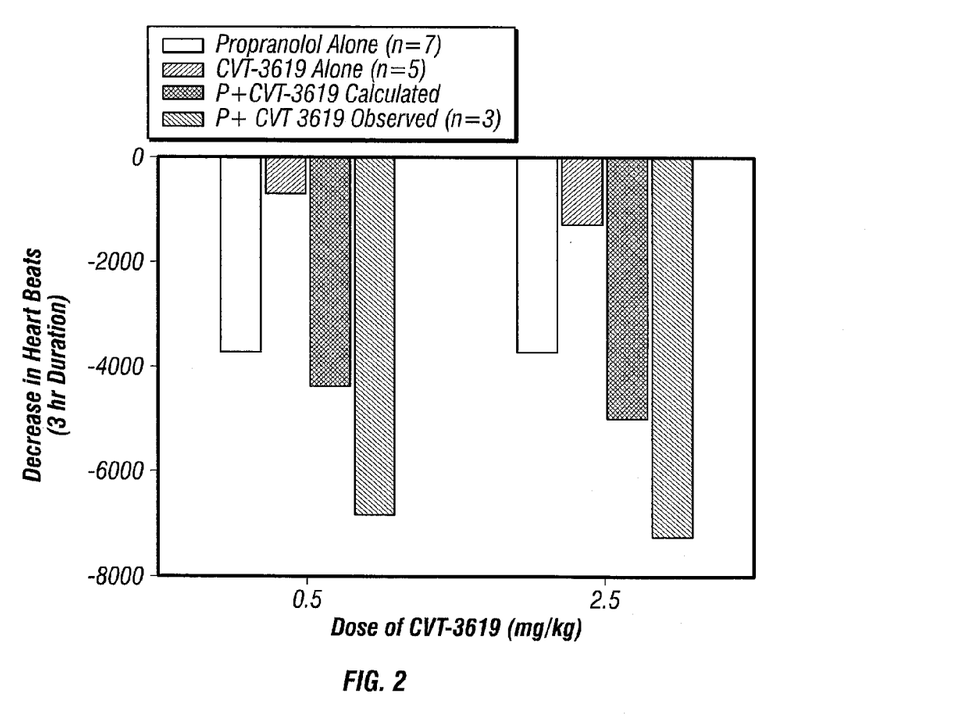
FIG. 2. Comparison of the effect of CVT-3619 alone and CVT-3619 in combination with propranolol on heart rate.

FIG. 2 shows the summary of data obtained from telemeterized awake rats. The data was quantified as area under the curve (AUC) and presented as a decrease in total number of heart beats for a 2 hour period of time caused by CVT-3619 (given ip) alone at two different doses and in the presence of propranolol (10 mg/kg, ip given 10 minutes prior to CVT-3619). The combination of CVT-3619 and propranolol results in a synergistic effect on heart rate, as the effect observed with combination is much greater than the calculated sum of the effect of each agent.

Figure 3:
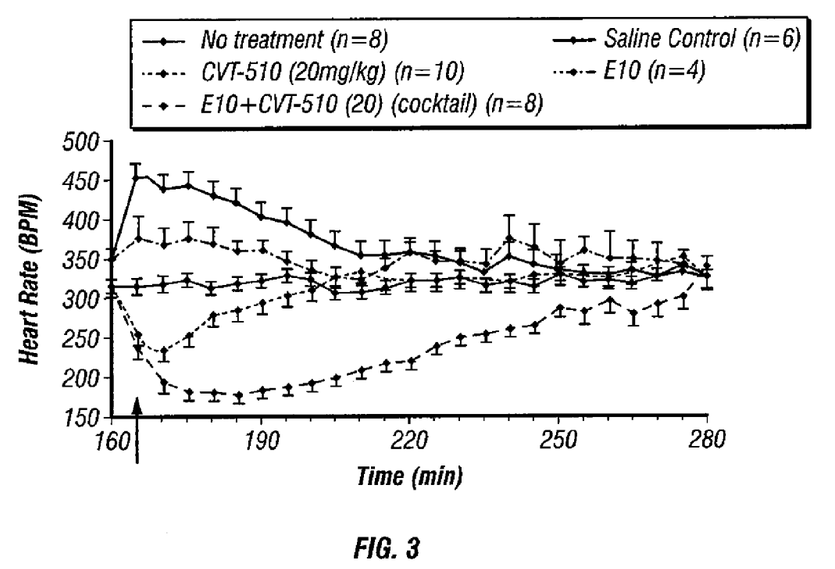
FIG. 3. Comparison of the effect of 20 µg/kg of CVT-510, 10 mg/kg of esmolol, and a combination of 20 µg/kg of CVT-510 and 10 mg/kg of esmolol on heart rate.

FIG. 3 shows the effect of CVT-510 and esmolol alone and given together as a mixture via ip injection to awake rats instrumented with telemetry radiotransmitters. CVT-510 at 20 μg/kg dose transiently lowers the heart rate below baseline levels whereas esmolol (10 mg/kg ip) only slightly reduces the increase in heart rate (which is caused by handling the animal). When the two agents are given in combination, the effect on heart rate is much greater. The combination not only increases the magnitude of the response but also increases the duration of bradycardia significantly.

Figure 4:
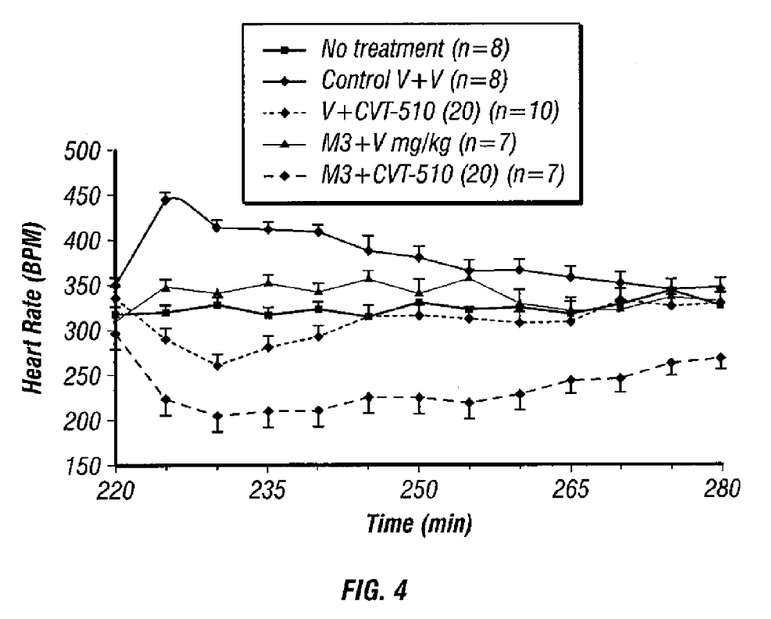
FIG. 4. Comparison of the effect of 20 µg/kg of CVT-510, 3 mg/kg of esmolol, and a combination of 20 µg/kg of CVT-510 and 3 mg/kg of esmolol on heart rate.

FIG. 4 shows the effect of CVT-510 alone and the effect when combined with the beta-blocker, Metoprolol, by observing the effect on heart rate in awake rats instrumented with telemetry radiotransmitters. CVT-510 (20 μg/kg, ip) slowed the heart rate in a dose dependent manner. In the presence of Metoprolol (3 mg/kg, ip), there was a greater lowering of heart rate.

Figure 5:
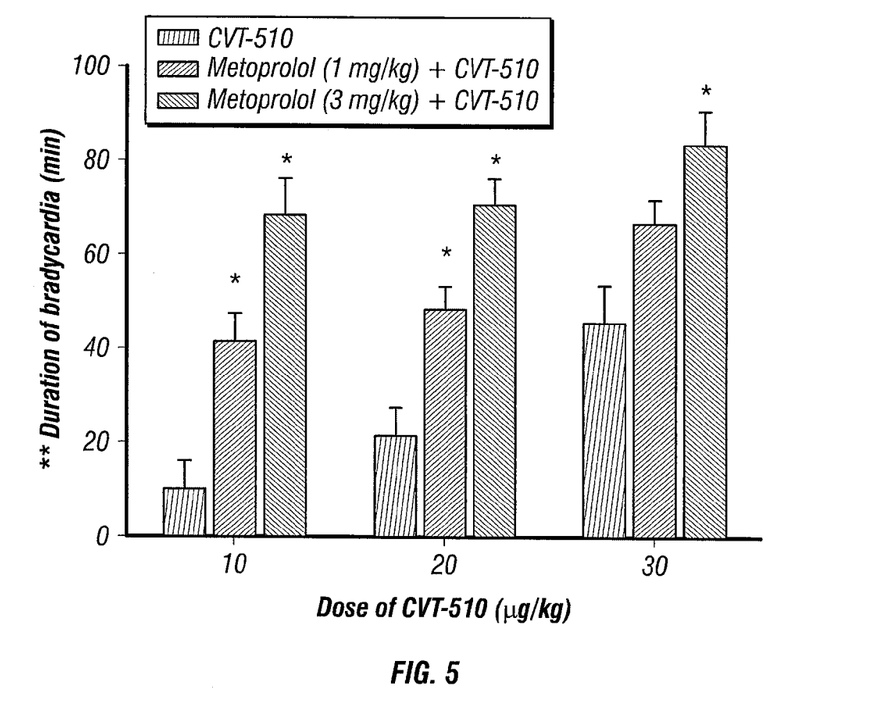
FIG. 5. Comparison of the effect of 10 µg/kg, 20 µg/Kg and 30 µg/kg doses of CVT-510, 1 mk/kg and 3 mg/kg of esmolol, and a combination of 20 µg/kg of CVT-510 and 1 and 3 mg/kg of esmolol on duration of Bradycardia.

FIG. 5. The duration of bradycardia caused by CVT-510 was analyzed by observing the time for the heart rate to return to 90% of pretreatment levels. In addition to the increase in magnitude of bradycardia, the combination of CVT-510 and metoprolol resulted in a significant increase in the duration of bradycardia as compared to that caused by CVT-510 alone.

Figure 6:
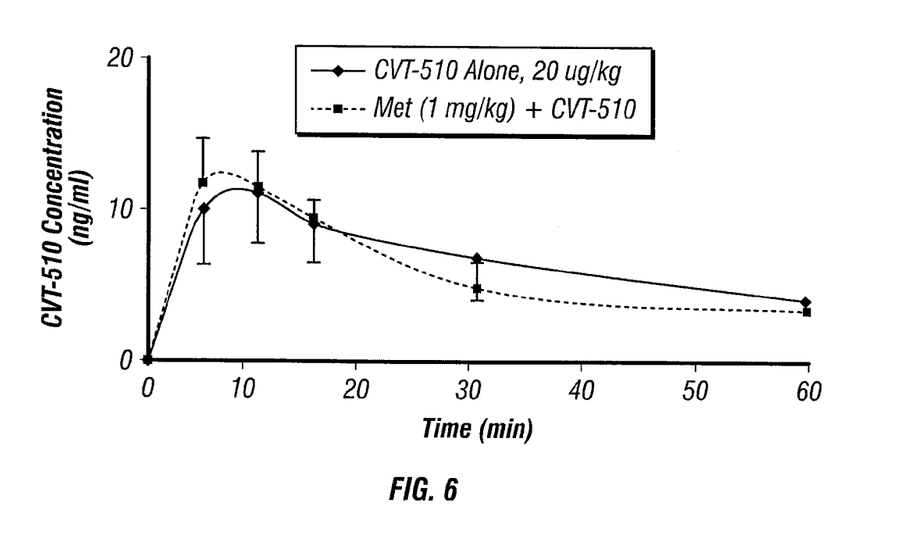
FIG. 6. Comparison of plasma levels of CVT-510 alone and a combination of CVT-510 and metoprolol.

FIG. 6: Plasma levels of CVT-510 were determined in the absence and presence of metoprolol in a separate group of animals (FIG. 6). Plasma levels of CVT-510 were found to be similar in both groups even though the slowing of heart rate caused by CVT-510 was greater in the presence of metoprolol indicating that the metabolism of CVT-510 was not changed in the presence of metoprolol.

Figure 7:
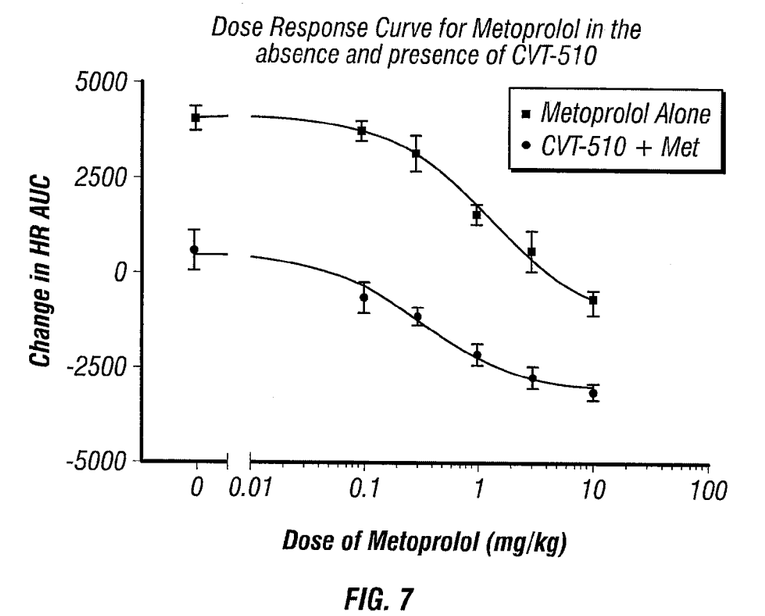
FIG. 7. Dose response curve for metoprolol in the absence and presence of CVT-510.

FIG. 7: To further investigate the mechanism of interaction of CVT-510 and beta-blockers, another series of experiments were performed in which the dose of CVT-510 was kept constant while the dose of metoprolol was varied. First a full dose response curve for metoprolol (0.1-10 mg/kg, ip) alone was obtained (FIG. 7, ■ symbols). In the second phase of the study, animals were implanted with osmotic pumps subcutaneously containing CVT-510. CVT-510 was delivered at a rate of 20 μg/kg/hr, which yielded plasma concentration of 7.5±1 ng/ml. Metoprolol dose response curve was repeated in these animals. In the presence of CVT-510, metoprolol dose response curve was shifted to the left and downward (FIG. 7, ● symbols).

Figure 8:
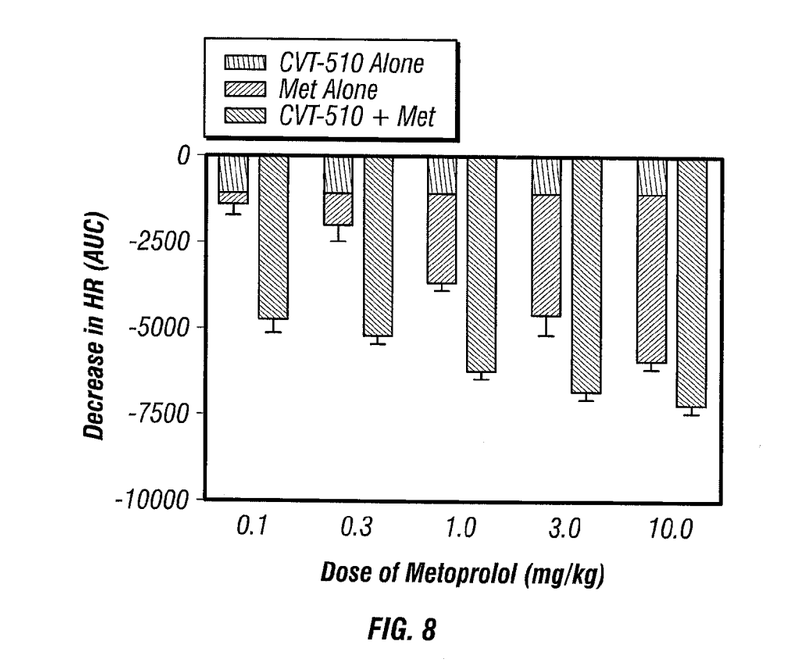
FIG. 8. This figure represents the data shown in FIG. 7.

FIG. 8: This figure represents the data shown in FIG. 7. The slowing of heart rate caused by CVT-510 and metoprolol was quantified by determining the area under the curve (AUC) for a period of 60 min for each treatment. The combined effect of CVT-510 and metoprolol on heart rate was found to be synergistic.

Figure 9:
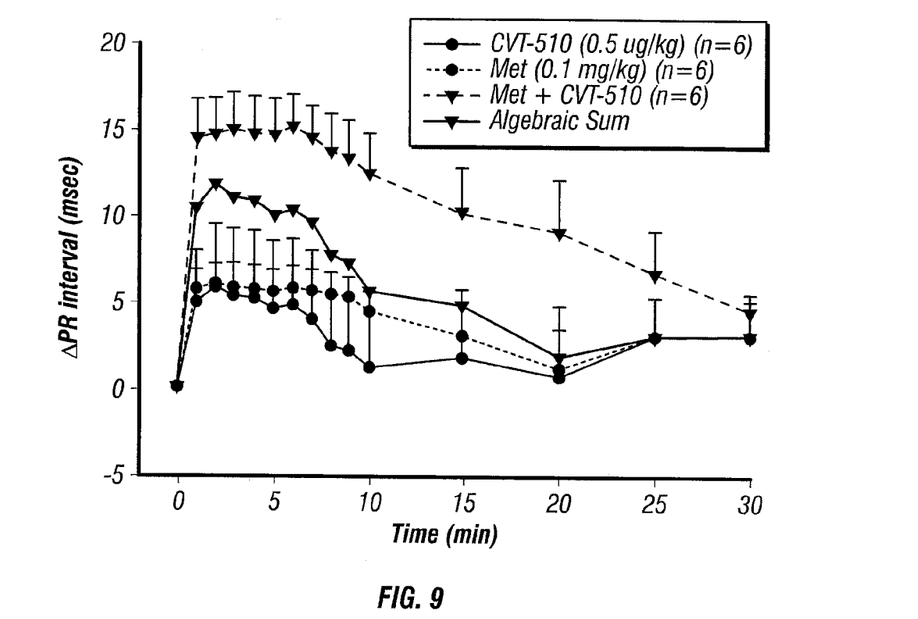
FIG. 9. Effect of CVT-510 (0.5 µg/kg) and metoprolol (0.1 mg/kg), which were given as an iv bolus, on PR interval FIG. 10. Effect of CVT-510 (0.5 µg/kg) and esmolol on PR interval
Figure 10:
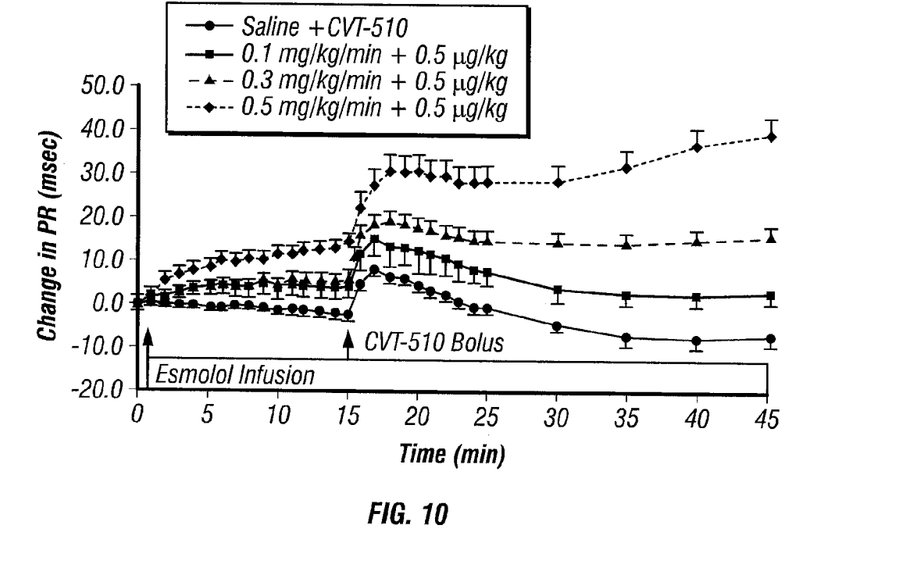

FIG. 9-10: Studies in anesthetized guinea pigs.

Male guinea pigs weighing 400-450 gm were obtained from Simonsen labs and housed in the institutional laboratory animal facility. Animals were anesthetized with isoflurane in the anesthetizing chamber. After determining (by toe pinch) that the animal is adequately anesthetized, the animals was intubated with an endotracheal tube and ventilated with isoflurane and oxygen mixture using anesthesia workstation. Using sterile equipment and aseptic technique, the right carotid artery was exposed and a catheter inserted for recording of blood pressure (BP). A quadripolar electrode catheter was introduced via the right jugular vein and positioned in the right atrium and ventricle for atrial and ventricular pacing. The hearts were paced at a constant rate (330-360 bpm) to eliminate the effect of heart rate variability between animals. Another catheter was inserted into the left jugular vein and positioned in the right atrium for the administration of drugs and saline. Subcutaneous needles were used as standard electrocardiographic leads to record the electrocardiogram (ECG). After completion of surgery and instrumentation, a 20 min equilibration period was allowed before beginning the experimental protocol. The data was recorded using Power Lab data acquisition system.

FIG. 9: CVT-510 (0.5 μg/kg) and metoprolol (0.1 mg/kg), which were given as an iv bolus, demonstrated an increased PR interval by 5 msec each in anesthetized guinea pigs. When the two agents were given in combination the PR interval was increased up to 15 msec. This is a synergistic effect, as the observed effect is more than the algebraic sum of the effect of each agent.

FIG. 10: Similar results were obtained when CVT-510 was given in the presence of with another beta-blocker, esmolol. Esmolol was administered at three different infusion rates. CVT-510 was given 15 minutes after starting the infusion of Esmolol. Effect of CVT-510 on PR interval was increased with increasing doses of esmolol. The duration of effect was significantly prolonged in a dose-dependent manner.

Thus, it has been demonstrated that the combination of a beta-blocker and $A_1$ agonist results in synergistic effects on heart rate in rats and PR interval in guinea pigs. The combined effect is dependent on the dose of either agent. That is, one can achieve similar responses by keeping one agent constant and varying the other. Various routes of administration of the drugs have been tried, and different combinations. For example, one drug has been administered 10 minutes after administration of the first, and 1 hour after administration of the first. The drugs have been given as a mixture, or given separately at the same time. The response varies in magnitude, but the overall effect is same. It has also been demonstrated that the combination is effective using both full $A_1$ adenosine receptor agonists and partial $A_1$ adenosine receptor agonists.

The combination has been shown to be effective in two different models.

1) Measurement of heart rate in awake rats, which is not a target for the $A_1$ agonists, but is used as a surrogate for the effect of $A_1$ agonists. The advantage of this model is that the high sympathetic tone seen in many forms of arrhythmias is simulated.
2) In anesthetized guinea pigs the AV nodal conduction method is useful for measuring the PR interval, which is the target of $A_1$ agonists. However, the sympathetic tone is blunted in this model due to anesthesia.

What is claimed is:

1. A pharmaceutical composition comprising a synergistic therapeutically effective minimal dose of an $A_1$ adenosine receptor agonist of Formula I and a therapeutically effective minimal dose of a beta blocker, and at least one pharmaceutically acceptable excipient, wherein the $A_1$ adenosine receptor agonist is a compound of Formula I:

Formula I wherein R₁ is 3-(R)-tetrahydrofuranyl,
wherein the beta blocker is esmolol, and
wherein the therapeutically effective amount of the compound of Formula I is from about 0.5 to 20 µg/kg and the therapeutically effective amount of esmolol is from about 0.1 to 10 mg/kg.

2. A pharmaceutical composition comprising a synergistic therapeutically effective minimal dose of an $A_1$ adenosine receptor agonist of Formula I and a therapeutically effective minimal dose of a beta blocker, and at least one pharmaceutically acceptable excipient, wherein the $A_1$ adenosine receptor agonist is a compound of Formula I:

Formula I wherein R₁ is 3-(R)-tetrahydrofuranyl,
wherein the beta blocker is metoprolol, and
wherein the therapeutically effective amount of the compound of Formula I is from about 0.5 to 20 µg/kg and the therapeutically effective amount of metoprolol is from about 0.1 to 10 mg/kg.

3. A pharmaceutical composition comprising a synergistic therapeutically effective minimal dose of an $A_1$ adenosine receptor agonist of Formula II and a therapeutically effective minimal dose of a beta blocker, and at least one pharmaceutically acceptable excipient, wherein the $A_1$ adenosine receptor agonist is a compound of Formula II:

Formula II wherein $R^1$ is (R)-2-hydroxycyclopentyl, X and Y are covalent bonds, $R^2$, $R^4$, and $R^5$ are hydrogen, and $R^3$ is 2-fluorophenyl, namely 2-{6-[((1R,2R)-2-hydroxycyclo-pentyl)amino]purin-9-yl}(4S,5S,3R)-5-[(2-fluorophenylthio)methyl]oxolane-3,4-diol (CVT-3619),
wherein the beta blocker is esmolol, and
wherein the therapeutically effective amount of the compound of Formula II is from about 0.1 to 200 mg/kg and the therapeutically effective amount of esmolol from about 0.01 to 100 mg/kg.

4. A pharmaceutical composition comprising a synergistic therapeutically effective minimal dose of an $A_1$ adenosine receptor agonist of Formula II and a therapeutically effective minimal dose of a beta blocker, and at least one pharmaceutically acceptable excipient, wherein the $A_1$ adenosine receptor agonist is a compound of Formula II:

Formula II wherein $R^1$ is (R)-2-hydroxycyclopentyl, X and Y are covalent bonds, $R^2$, $R^4$, and $R^5$ are hydrogen, and $R^3$ is 2-fluorophenyl, namely 2-{6-[((1R,2R)-2-hydroxycyclo-pentyl)amino]purin-9-yl}(4S,5S ,3R)-5-[(2-fluorophenylthio)methyl]oxolane-3,4-diol (CVT-3619),
wherein the beta blocker is metoprolol, and
wherein the therapeutically effective amount of the compound of Formula II is from about 0.1 to 200 mg/kg and the therapeutically effective amount of metoprolol from about 0.01 to 100 mg/kg.

5. A pharmaceutical composition comprising a synergistic therapeutically effective minimal dose of an $A_1$ adenosine receptor agonist of Formula II and a therapeutically effective minimal dose of a beta blocker, and at least one pharmaceutically acceptable excipient, wherein the $A_1$ adenosine receptor agonist is a compound of Formula II:

Formula II wherein $R^1$ is (R)-2-hydroxycyclopentyl, X and Y are covalent bonds, $R^2$, $R^4$, and $R^5$ are hydrogen, and $R^3$ is 2-fluorophenyl, namely 2-{6-[((1R,2R)-2-hydroxycyclo-pentyl)amino]purin-9-yl}(4S ,5S,3R)-5-[(2-fluorophenylthio)methyl]oxolane-3,4-diol (CVT-3619),
wherein the beta blocker is propranolol, and
wherein the therapeutically effective amount of the compound of Formula II is from about 0.1 to 200 mg/kg and the therapeutically effective amount of propranolol from about 0.01 to 100 mg/kg.

* * * * *